United States Patent
Mahesh et al.

(10) Patent No.: US 8,019,626 B2
(45) Date of Patent: Sep. 13, 2011

(54) INTEGRATED AND INTUITIVE DISPLAY OF CLINICAL INFORMATION

(75) Inventors: Prakash Mahesh, Hoffman Estates, IL (US); Murali Kariathungal, Hoffman Estates, IL (US); Sukhdeep Gill, Ontario (CA); Christopher Janicki, Sleepy Hollow, IL (US)

(73) Assignee: General Electric Company, Schenectady, NY (US)

( * ) Notice: Subject to any disclaimer, the term of this patent is extended or adjusted under 35 U.S.C. 154(b) by 117 days.

(21) Appl. No.: 11/944,060

(22) Filed: Nov. 21, 2007

(65) Prior Publication Data

US 2009/0132588 A1    May 21, 2009

(51) Int. Cl.
G06Q 100/00 (2006.01)
G06Q 50/00 (2006.01)
A61B 5/00 (2006.01)
G06F 19/00 (2011.01)

(52) U.S. Cl. .............................................. 705/3; 705/2
(58) Field of Classification Search .................... 705/2–3
See application file for complete search history.

(56) References Cited

U.S. PATENT DOCUMENTS

| | | | | |
|---|---|---|---|---|
| 7,058,901 | B1 * | 6/2006 | Hafey et al. .................... | 715/792 |
| 7,273,454 | B2 | 9/2007 | Raymond et al. | |
| 2002/0082484 | A1 * | 6/2002 | Baba et al. .................... | 600/300 |
| 2007/0292012 | A1 * | 12/2007 | Brandon et al. .............. | 382/128 |

OTHER PUBLICATIONS http://www.isitepacs.medical.philips.com/pacs/iSite_Radiology.php.
Philips Radiology Informatics, iSite Radiology, Radiology Reading Station, "A More Efficient Way to Work," Netherlands, Jan. 2006.

* cited by examiner

Primary Examiner — Luke Gilligan
Assistant Examiner — Joy Chng
(74) Attorney, Agent, or Firm — McAndrews, Held & Malloy, Ltd.; Michael A. Dellapenna

(57) ABSTRACT

Certain embodiments of the present invention provide a system for clinical review of a patient comprising: a plurality medical studies relating to a medical history of the patient, each of said plurality of medical studies comprising a representation; a user interface for permitting a user to interact with said representations; a chronology of said representations displayable through said user interface, wherein each of said representations is selectable by said user to form a selected chronological medical study; and a plurality of relevant representations displayable through said user interface, said plurality of relevant representations automatically generated based at least in part on said selected chronological medical study and at least one relevance criterion, wherein each of said plurality of relevant representations is selectable to form a selected relevant medical study. In an embodiment, the system further comprises at least one thumbnail image displayed in said user interface, said at least one thumbnail image corresponding to a series of images in said selected relevant medical study, wherein said at least one thumbnail image is selectable to display said series of images in said selected relevant medical study.

20 Claims, 8 Drawing Sheets

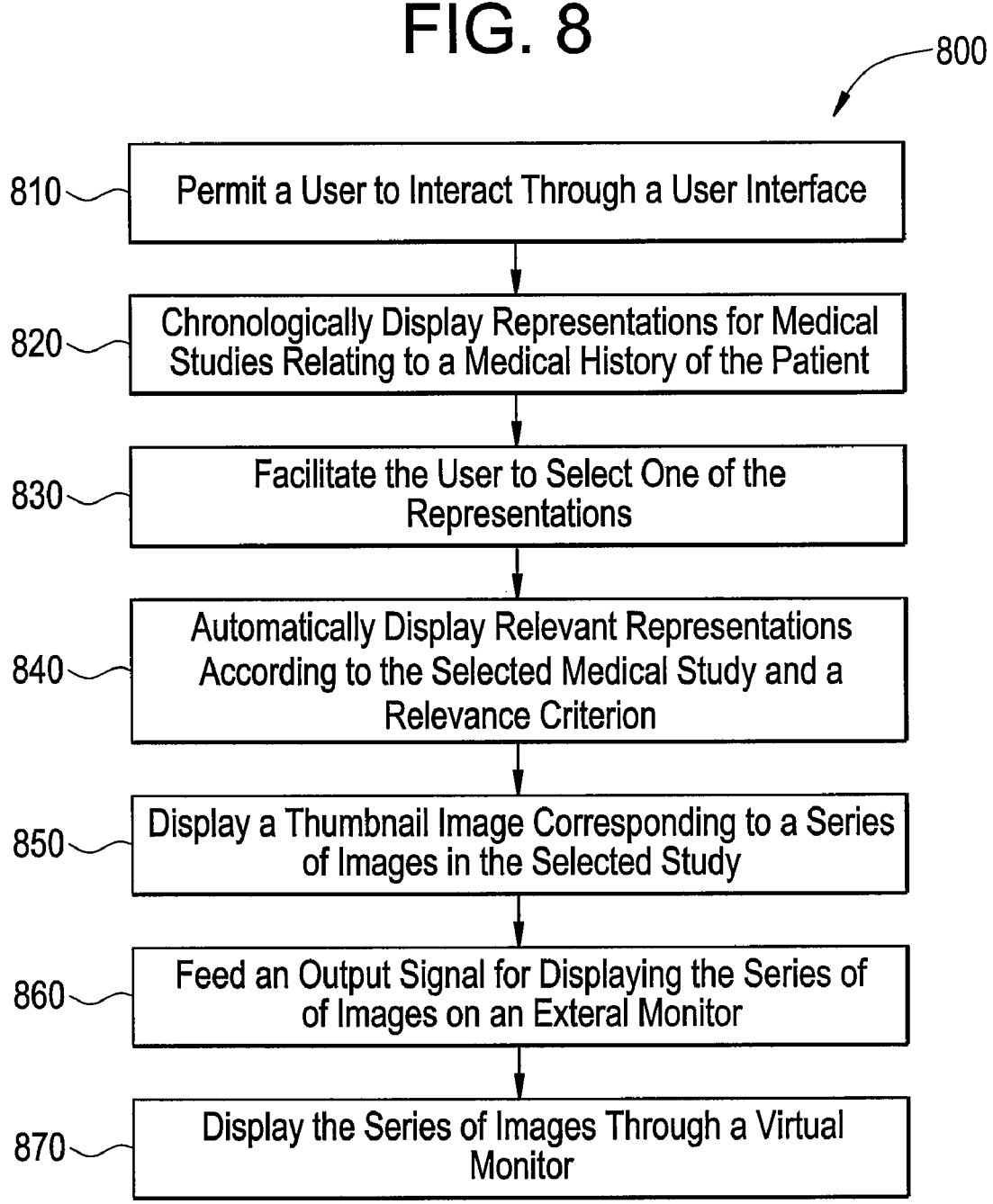

INTEGRATED AND INTUITIVE DISPLAY OF CLINICAL INFORMATION

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present application relate generally to dynamic display of clinical information through a user interface. Particularly, certain embodiments relate to chronological and relevant displays of medical studies in an intuitive and fluid manner.

When reviewing a patient's medical history, a reviewing clinician is faced with managing a potentially large amount of information. It should be understood that a patient's medical history may also include presently generated studies that are in a condition for clinical review. For a given patient, there may be studies spannig over a period of months or years. The studies may cover a variety of conditions and/or body parts. The studies may pertain to various clinical areas—e.g., radiology, cardiology, laboratory exams, neurology, pathology, oncology, etc. For radiology and other medical imaging applications, the studies may be generated through various modalities—e.g., CT scan, fluoroscopy, tomography, ultrasound, MRI, etc.

Furthermore, there may be layers of information for each study—e.g., various levels of information such as metadata, high-level study information, and underlying study data. The underlying data may also be stored in a variety of forms—e.g., linked database information, images, movies, text, etc. Given the potentially vast and diverse amount of information for any given patient, a reviewing clinician is faced with a difficult task.

The various patient studies, as a group may be considered horizontal patient information. For a given study, the various layers of information may be considered vertical information.

For a given patient review, a clinician may have to select among the horizontal patient information to efficiently access relevant patient studies. Further, the clinician may desire to efficiently "drill-down" through the vertical layers of a given patient study. It may be inefficient to provide a work-flow for the clinician that requires the manual integration of various data sources, data management applications, and data monitoring scenarios.

Thus, there is a need for efficient management of clinical patient information. There is a need for the ability for a clinician to intuitively browse, select, and review the horizontal and vertical patient information. Furthermore, there is a need for the clinician to manage in an integrated manner, both horizontally and vertically, the patient history information.

BRIEF SUMMARY OF THE INVENTION

Certain embodiments of the present invention provide a system for clinical review of a patient comprising: a plurality medical studies relating to a medical history of the patient, each of said plurality of medical studies comprising a representation; a user interface for permitting a user to interact with said representations; a chronology of said representations displayable through said user interface, wherein each of said representations is selectable by said user to form a selected chronological medical study; and a plurality of relevant representations displayable through said user interface, said plurality of relevant representations automatically generated based at least in part on said selected chronological medical study and at least one relevance criterion, wherein each of said plurality of relevant representations is selectable to form a selected relevant medical study. In an embodiment, the system further comprises at least one thumbnail image displayed in said user interface, said at least one thumbnail image corresponding to a series of images in said selected relevant medical study, wherein said at least one thumbnail image is selectable to display said series of images in said selected relevant medical study. In an embodiment, the system further comprises an external monitor output for feeding a display of said series of images in said selected relevant medical study to an external monitor. In an embodiment, the system further comprises at least one virtual monitor displayable in said user interface, said series of images in said selected relevant medical study displayable in said at least one virtual monitor. In an embodiment, the user interface permits said user to drag and drop said at least one thumbnail image into said at least one virtual monitor. In an embodiment, each of at least a portion of said representations comprise corresponding preview information, wherein said user initiates a preview interaction with one of said representations to view said corresponding preview information in the proximate vicinity of said preview interaction. In an embodiment, the user interface is dynamically configurable according to at least one of: a thumbnail scale for adjusting a size of said at least one thumbnail image, and a paging selection for paging through said representations. In an embodiment, the plurality of medical studies comprise a radiology study.

Certain embodiments of the present invention provide a method for clinical review of a patient comprising: permitting a user to interact through a user interface, chronologically displaying in said user interface chronological representations for each of a plurality medical studies relating to a medical history of the patient, facilitating said user to select one of said chronological representations to form a selected chronological medical study; and automatically displaying a plurality of relevant representations through said user interface based at least in part on said selected chronological medical study and at least one relevance criterion, wherein each of said plurality of relevant representations is selectable to form a selected relevant medical study. In an embodiment, the method further comprises displaying at least one thumbnail image in said user interface, said at least one thumbnail image corresponding to a series of images in said selected relevant medical study, wherein said at least one thumbnail image is selectable to display said series of images in said selected relevant medical study. In an embodiment, the method further comprises feeding an output signal for displaying said series of images in said selected relevant medical study to an external monitor. In an embodiment, the method further comprises displaying said series of images in said selected relevant medical study through at least one virtual monitor. In an embodiment, the method further comprises facilitating said user to drag and drop said at least one thumbnail image into said at least one virtual monitor. In an embodiment, the method further comprises displaying preview information for at least one of said chronological representations and at least one of said relevant representations in response to a user-initiated preview interaction. In an embodiment, the method further comprises facilitating dynamic configuration of said user interface according to at least one of: a thumbnail scale for adjusting a size of said at least one thumbnail image, and a paging selection for paging through said representations. In an embodiment, the plurality of medical studies a radiology study.

Certain embodiments of the present invention provide a computer-readable storage medium including a set of instructions for a computer, the set of instructions comprising: an interaction routine for permitting a user to interact through a user interface, a chronological display routine for chronologically displaying in said user interface chronological representations for each of a plurality medical studies relating to a medical history of the patient, a selection routine for facilitating said user to select one of said chronological representations to form a selected chronological medical study; and a relevance routine for automatically displaying a plurality of relevant representations through said user interface based at least in part on said selected chronological medical study and at least one relevance criterion, wherein each of said plurality of relevant representations is selectable to form a selected relevant medical study. In an embodiment, the set of instructions further comprise a thumbnail display routine for displaying at least one thumbnail image in said user interface, said at least one thumbnail image corresponding to a series of images in said selected relevant medical study, wherein said at least one thumbnail image is selectable to display said series of images in said selected relevant medical study. In an embodiment, the set of instructions further comprise a virtual monitor display routine for displaying said series of images in said selected relevant medical study through at least one virtual monitor. In an embodiment, the set of instructions further comprise a preview display routine for displaying preview information for at least one of said chronological representations and at least one of said relevant representations in response to a user-initiated preview interaction.

BRIEF DESCRIPTION OF SEVERAL VIEWS OF THE DRAWINGS

FIG. 3 shows a representative screen shot of a user interface for displaying patient studies, according to an embodiment of the present invention.

FIG. 7 shows a representative screen shot of a user interface for displaying patient studies, according to an embodiment of the present invention.

FIG. 8 shows a flowchart for a method of review of patient studies, according to an embodiment of the present invention.

Figure 1:
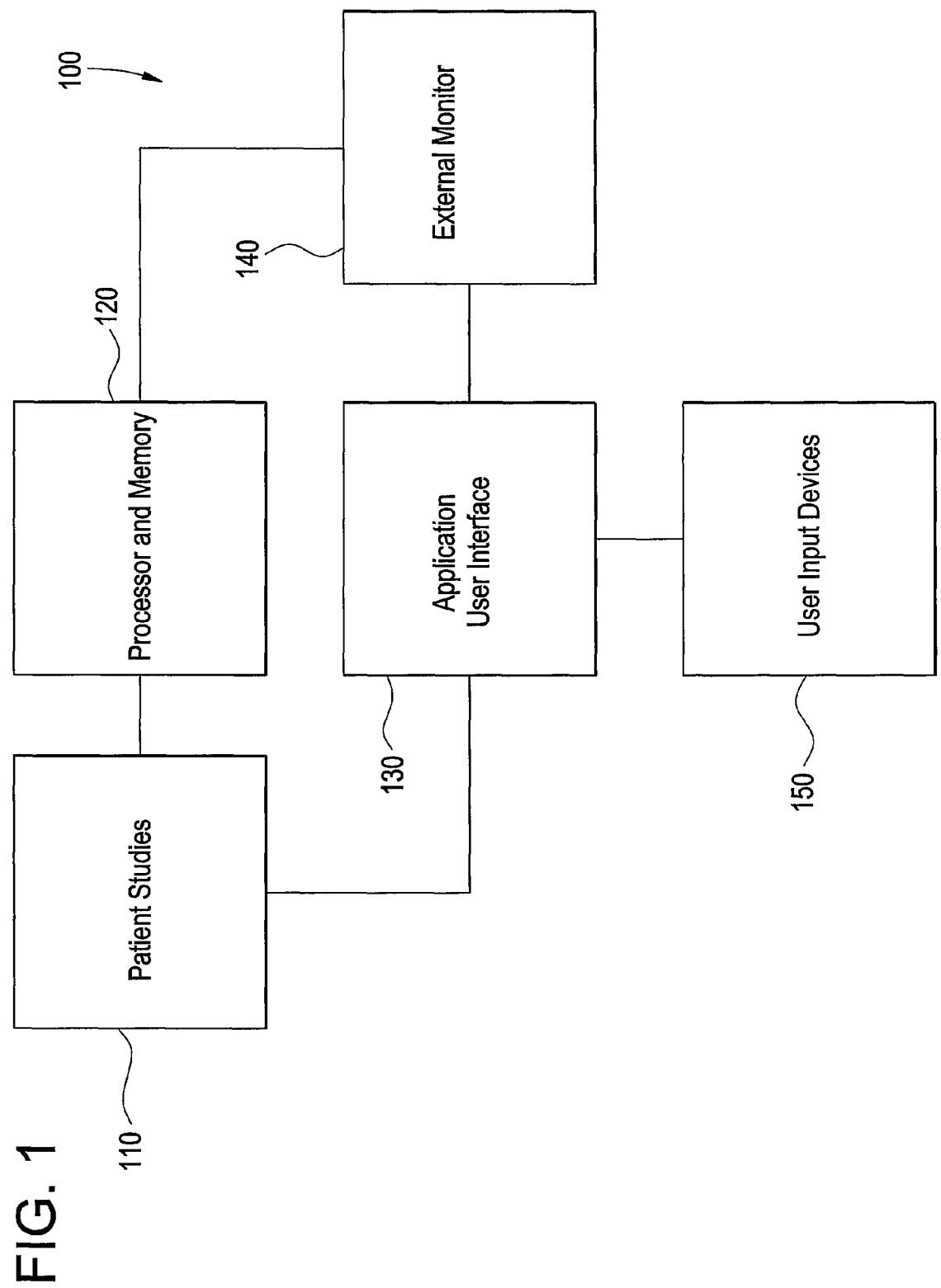
FIG. 1 shows a system for displaying patient studies, according to an embodiment of the present invention.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings. Further, some figures may be representations of the type of display and/or output associated with methods and systems of the present invention, in accordance with one or more embodiments.

DETAILED DESCRIPTION OF THE INVENTION

FIG. 1 shows a system 100 for displaying patient studies, according to an embodiment of the present invention. The system 100 may include patient studies 110, a processor and memory 120, an application and user interface 130, an external monitor 140, and/or user input devices 150. The system 100 may be incorporated, at least in part, into an enterprise system, such as a RIS, or PACS system.

The patient studies 110 may include current and historical patient studies. The patient studies may reside on one or more local or network accessible memories. The studies may be generated according to various clinical purposes: e.g., radiology; a cardiology, pathology, neurology, and laboratory examination and/or the like. Each study may include various layers (vertical information) of data—e.g., top-level, meta-data, and low-level data. The top-level or metadata may include various information including the date of the study, the modality of the study, the procedure, the patient condition, the treating physician, health insurance information, the body part, etc. The low-level data may be in various forms—e.g., text, linked database, image, movie, etc. For imaging studies (e.g., radiology), the study may include image and/or movie data.

The processor and memory 120 may be capable of executing/supporting the application and user interface 130. The memory may include a computer readable storage medium including various sets of instructions. The processor and memory 120 may also support display of data on an external monitor 140. The processor and memory 120 may be capable of importing/exporting the patient studies 110. The processor and memory 120 may also be capable of processing, driving, and otherwise supporting data displayed on the external monitor 150.

The processor and memory 120 may be capable of executing/supporting the application and user interface 130. The memory may include a computer readable storage medium including various sets of instructions. The processor and memory 120 may also support display of data on an external monitor 140. The processor and memory 120 may be capable of importing/exporting the patient studies 110. The processor and memory 120 may also be capable of processing, driving, and otherwise supporting data displayed on the external monitor 140.

Figure 2:
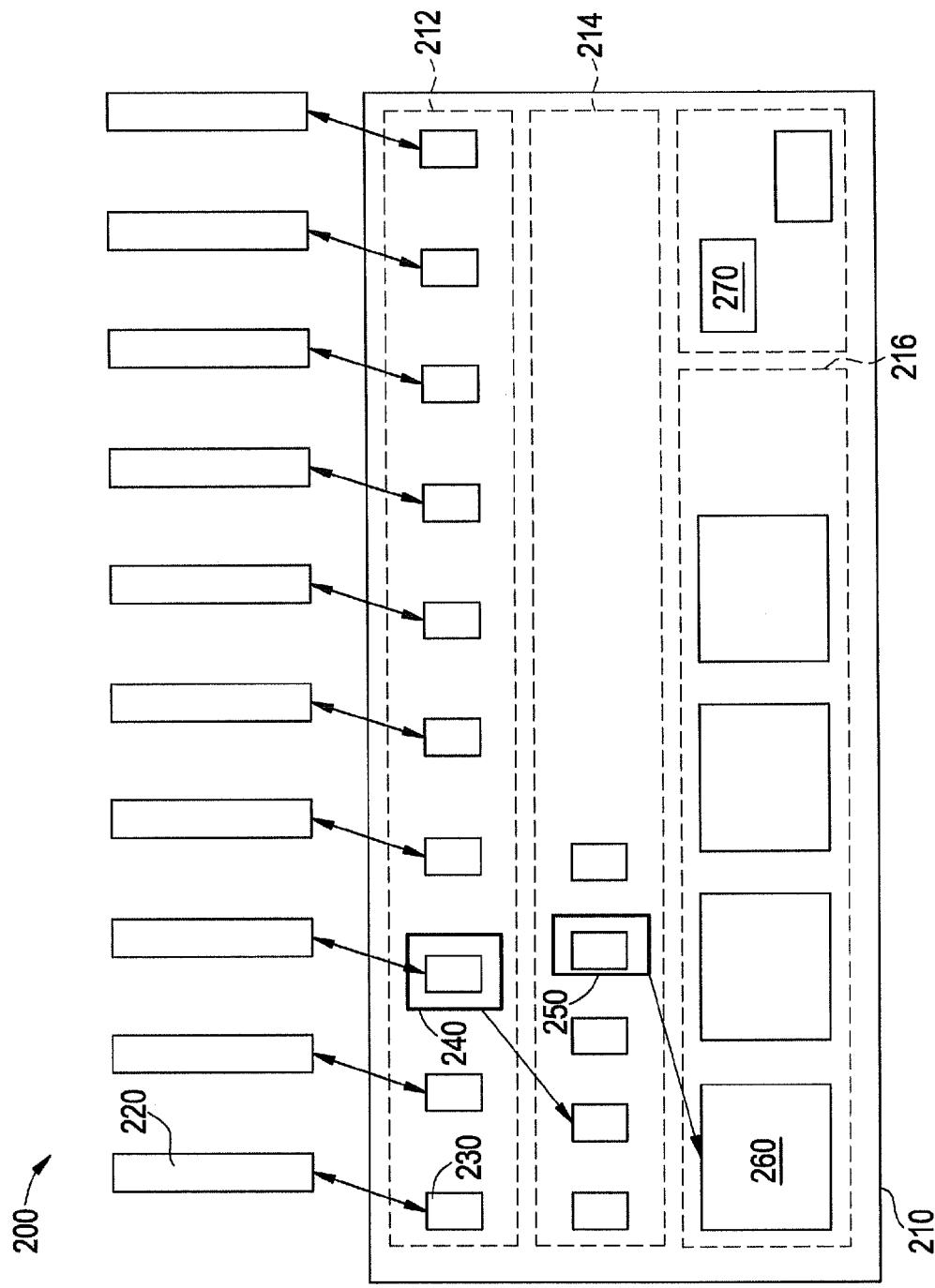
FIG. 2 shows a system for displaying patient studies, according to an embodiment of the present invention.

FIG. 2 shows a system 200 for displaying patient studies, according to an embodiment of the present invention. The system 200 may include a user interface 210, patient medical studies 220, corresponding representations 230 for the medical studies 230, a view of a chronology of the representations 212, a view of relevant representations 214, a view of thumbnail image(s) 216, a view of virtual monitor(s), a selected chronological medical study 240, a selected relevant medical study 250, thumbnail image(s) 260, and virtual monitor(s) 270.

The user interface 210 may be an integrated view of various components of system 200 as described herein. The user interface 210 may permit a user (e.g., radiologist) to manage and interact with various patient medical studies and the representations thereof 220, 230. The user may also interact with vertically integrated study data such as image series and thumbnails thereof 260. The user may use user interface devices (e.g., devices 150) to interact. The interface may dynamically display information as described herein. The interface 210 inlay assist in management of moritor display (both virtual and external). The interface 210 may be displayed on a PACS workstation. As will be further described, the interface 210 may allow the user to intuitively manage both horizontal and vertical information relating to the patient medical studies 220. The user interface 210 may include characteristics associated with a window-type interface (e.g., maximize, minimize, scale, close, display options, preferences, save, open, print, copy, paste, etc.).

For ease of discussion, the patient medical studies 220 may be understood to include a corresponding representation 230. Even though the representation 230 may not be a permanent part of the study 220, it may be temporarily associated with the study 220. As further illustrated in FIGS. 3-7, the representations 230 may include various visual information including: icons, dates, and modalities. The icons may pertain to the type of study (e.g., radiology, cardiology, etc.), the modality (e.g., CT scan, MRI, etc.) and other clinically useful information. Additionally, the representations may include textual information proximately displayed, such as the date of the study, the type of modality, the work-flow status, and other clinically useful information. Furthermore, the representations may include color coding information that may correspond to work-flow status, and other clinically useful information as described.

The user may interact with the representations in various ways. For example, the user may select a representation through a mouse click or similar. Such a selection may result in a selected representation. The user may also interact to preview information related to a medical study 220 by clicking, rolling over with a mouse, right clicking, etc. Various interactions may dynamically adjust the display of the representations themselves. For example, preview information may pop-up in a proximate vicinity of a representation 230 in response to a preview interaction (as illustrated, e.g., in FIG. 6). Preview information may include date and time information, a thumbnail image of study image data, a report summary, and/or the like. Also representation may grow in size (e.g., FIG. 5), or otherwise change a characteristic (e.g., color) in response to selection. If there is a current exam (e.g., recently performed procedure that is subject to clinical review), the current exam may be visually represented as current (e.g., FIGS. 3-7).

the chronological view of the representations 212 may show a chronology of the representations 230, and may be displayable through the user interface 210. The chronology 212 may include all available studies (or a portion thereof) pertaining to a given patient. A user may be able to page through the chronology of representations 212 (e.g., FIGS. 3-7) if they do not fit within the user interface at one time. Another option may use multiple rows of representations 230. There may be calendar information visually organizing the representations 230 (e.g., FIGS. 3-7).

Each of the representations 230 may be selected by the user to form a selected chronological medical study 240. Once selected, the representation may provide visual feedback to the user to indicate selection—e.g., color or size change. Once selected, the view of relevant representations 214 may be automatically populated with the selected chronological medical study 240 and other relevant studies. The relevant studies may be determined according to relevance criteria. The relevance criteria may be processed through one or more algorithms. Examples of relevance criteria include: studies in the last six months, same patient, same body part, same study type, same treating physician, same modality, and/or the like. The relevant studies may be represented by representations, similar to those in the chronological view. The user may further select one of the relevant studies, similar to selection of the chronological representations. Once a relevant study is selected, it may form a selected relevant medical study 250. The selected relevant medical study 250 may default to correspond to the selected chronological medical study 240.

Especially if the study contains image data, the interface may display one or more thumbnail images 260 in the view of thumbnail images 216 corresponding to the selected medical study 250. The size of the thumbnail images 216 may be scaled through a scale selector to various sizes (e.g., FIG. 7). The thumbnail images 216 may represent image data of the selected relevant medical study 250. For example, the thumbnail 260 may represent the first image of a sequence of images. Multiple thumbnails 260 may represent subsequent images in a series, or may represent an image from multiple series. The user may perform a preview interaction to view preview information in the proximate vicinity of the thumbnail 260 in a similar manner as discussed above.

The virtual monitor 270 may include one or more virtual monitors. The display for virtual monitors 270 may be hidden or displayed. The virtual monitor 270 may provide a place in the user interface 210 to display image and cine for images or series of images in the selected relevant medical study 250. A user may view image and cine information by selecting a representation or a thumbnail image 260. For example, the user may be able to double click or similar to cause the image information to appear in the virtual monitors 270. Additionally, the user may drag and drop the representations or thumbnail images 260 into the virtual monitors 270. More than one image/cine may be displayed in a corresponding number of virtual monitors 270. The user may drag and drop from one virtual monitor to the next to configure display of the image/cine information.

Additionally, a feed may be provided to one or more external monitors. The configuration of external monitors may be mirrored in the virtual monitors 270. It may be possible to configure external monitors by adjusting the configuration of the virtual monitors.

Figure 3:
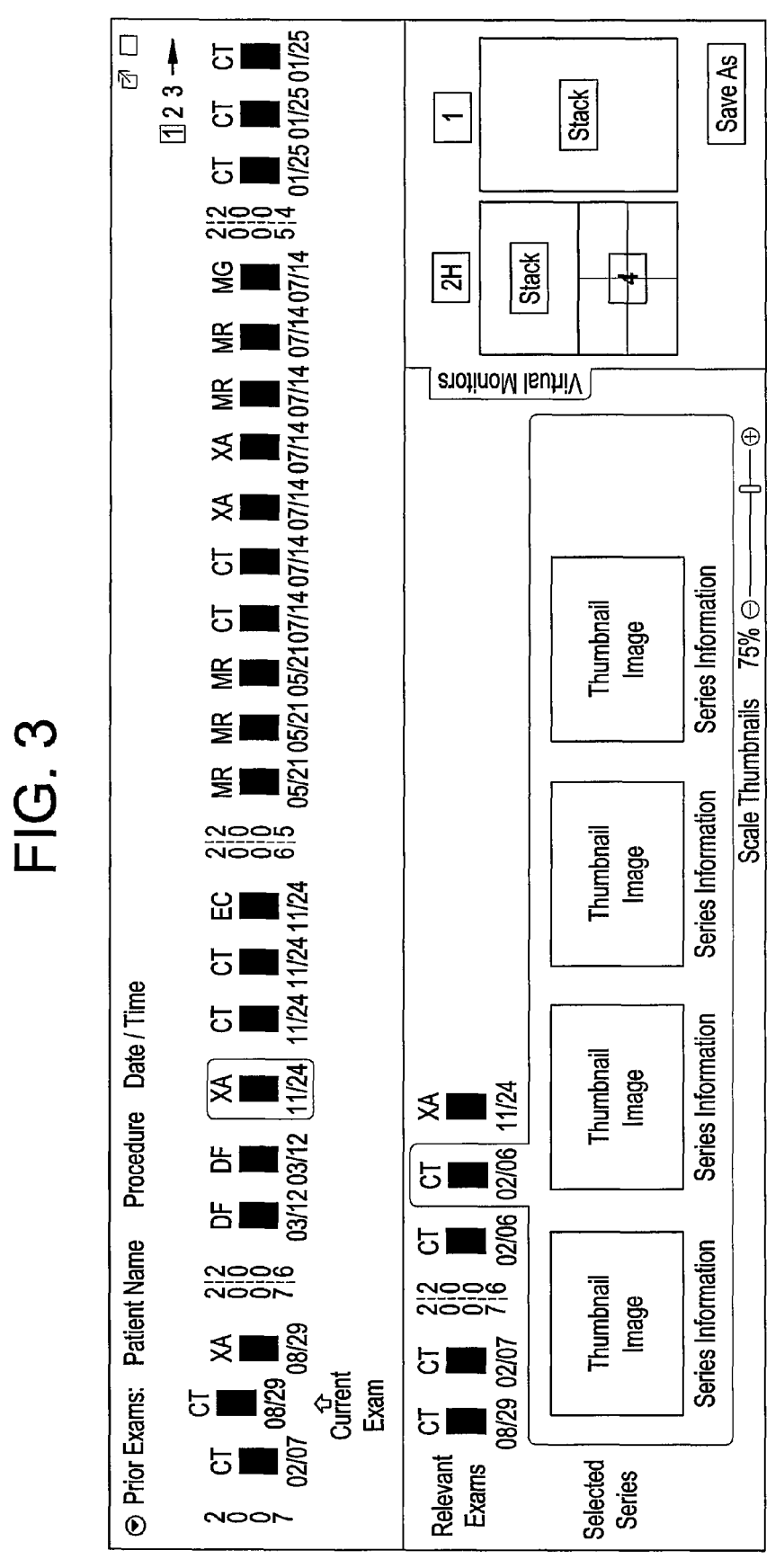
Figure 4:
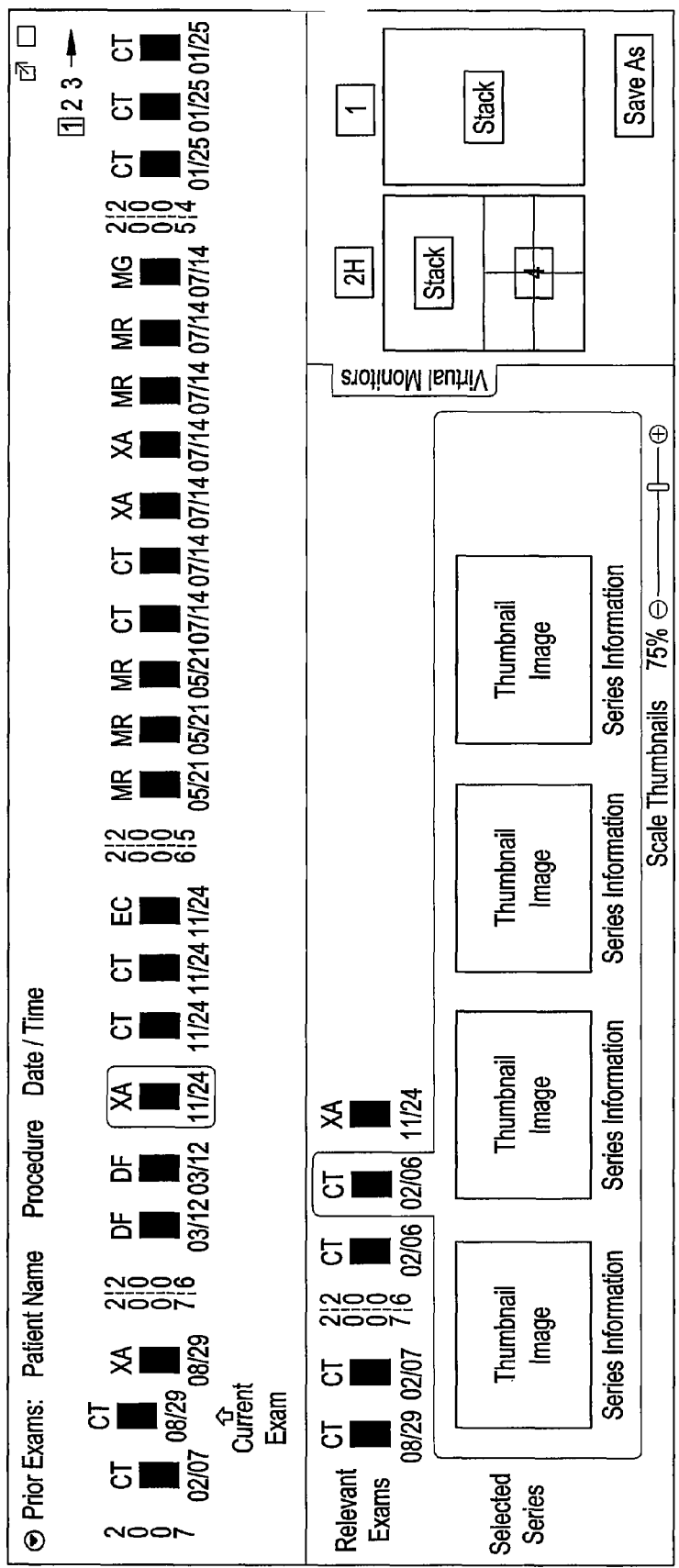
FIG. 4 shows a representative screen shot of a user interface for displaying patient studies, according to an embodiment of the present invention.
Figure 5:
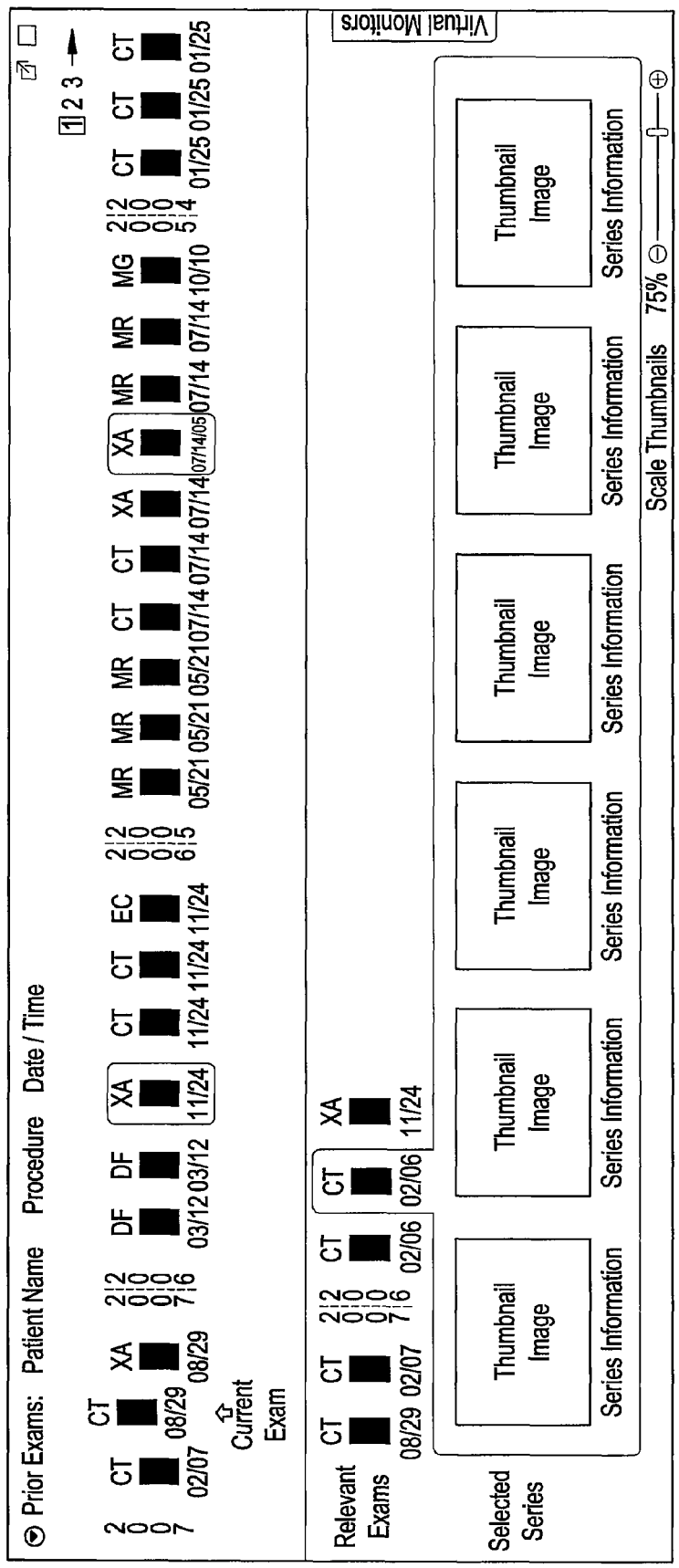
FIG. 5 shows a representative screen shot of a user interface for displaying patient studies, according to an embodiment of the present invention.
Figure 6:
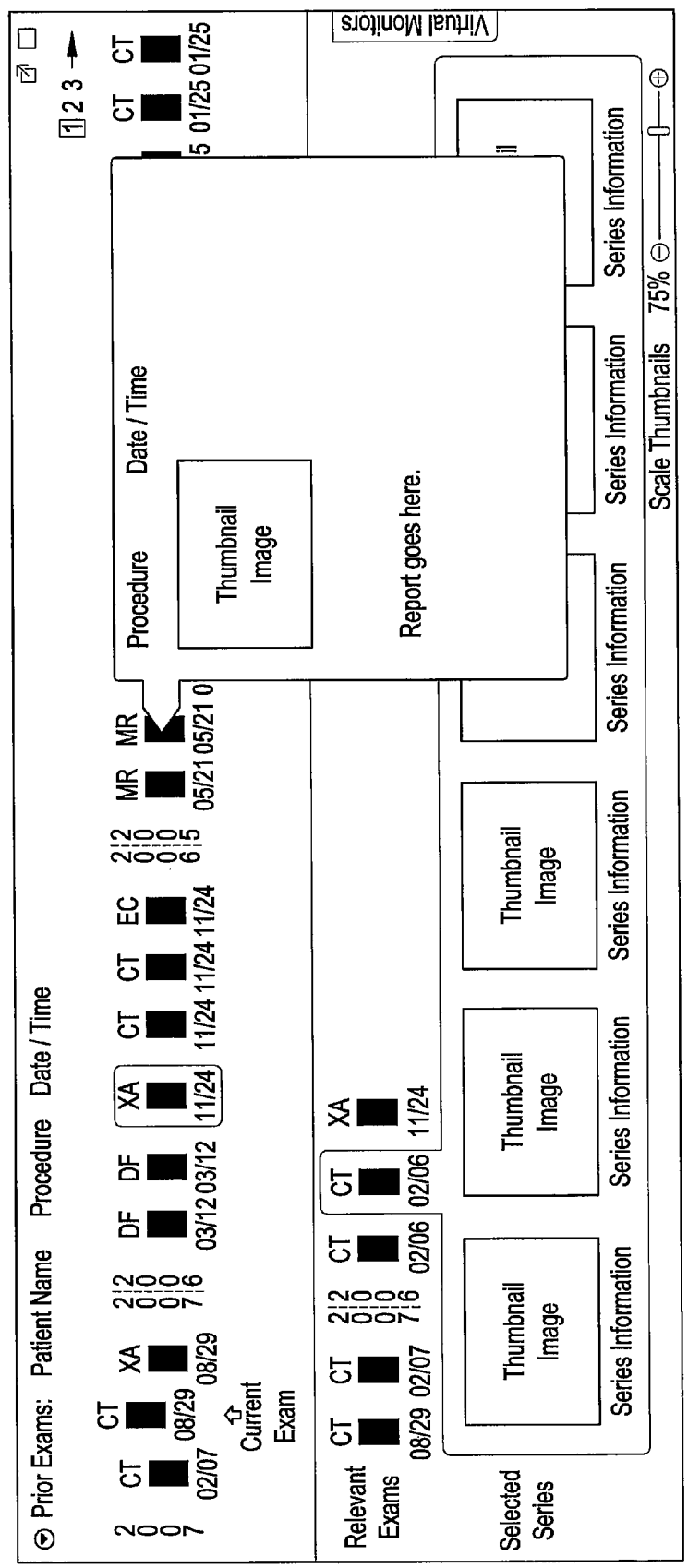
FIG. 6 shows a representative screen shot of a user interface for displaying patient studies, according to an embodiment of the present invention.
Figure 7:
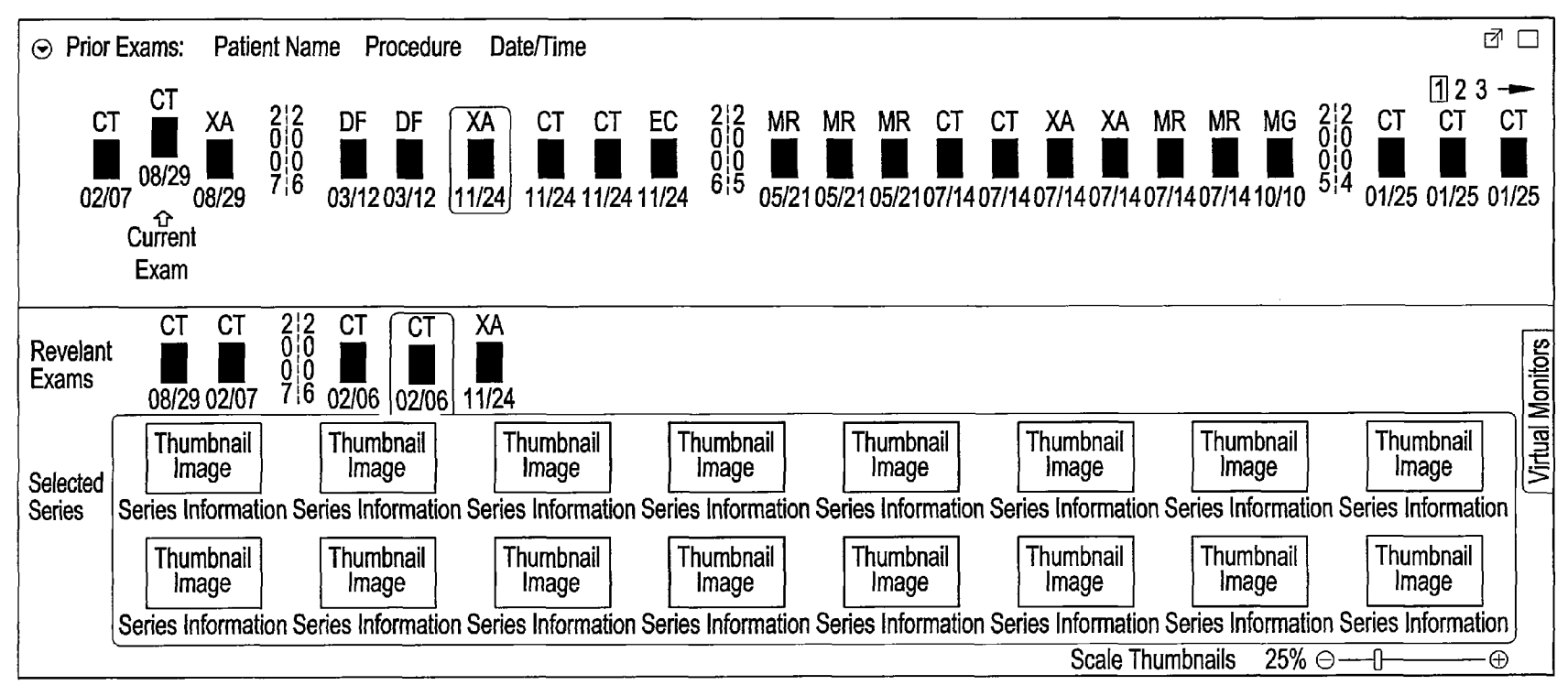

FIGS. 3-7 show representative screen shots of a user interface for displaying patient studies, according to an embodiment of the present invention. FIG. 3 shows an example of the interface when patient studies are loaded and displayed. FIG. 4 shows an example of an interface using a virtual monitor tab (that may be maximized and minimized). FIG. 5 shows an example of an interface where a representation is enlarged in result to a user in result from a user interaction. FIG. 6 shows an example of preview information shown in the proximate vicinity of a representation in response to a preview interaction. FIG. 7 shows an example of thumbnail scalability.

FIG. 8 shows a flowchart for a method 800 to review of patient studies, according to an embodiment of the present invention. The steps of the method 800 may be performable, for example, by a system, such as systems 100, 200, at least in part. Furthermore, the steps of method 800 may be performable in a different order, or some steps may be omitted. The steps may be performed in a different order according to design and/or clinical preferences. Method 800, or a portion thereof, may be performable by one or more processing units. Method 800, or a portion thereof, may be performable by software, hardware, and/or firmware. Method 800, or a portion thereof, may also be expressible through a set of instructions stored on one of more computer-readable storage media, such as RAM, ROM, EPROM, EEPROM, optical disk, magnetic disk, magnetic tape, and/or the like.

At step 810 a user is permitted to interact through a user interface. The user interface may be part of an application, or may be the portal to an application. The user may wish to evaluate a patient's medical history. The user may, for example, enter data corresponding to a given patient to draw up the patient's medical records. At step 820, the user interface presents a chronological display of representations that correspond to medical studies in the patient's history. At step 830, the user interface facilitates the user to select one of the representations. The selected representation may form a selected chronological medical study. Visual feedback may be provided to the user to indicate that there has been a selection. As another option, the user interface may facilitate the user to perform a preview interaction on the representation—e.g., right click, single click, mouse-over, etc. The preview interaction may signal to the user interface to display preview information relating to the study of interest. The preview information may be displayed in the proximate vicinity of the representation, or elsewhere.

If there is a selected chronological medical study, the method may proceed to step 840, when the interface automatically displays a set of relevant representations. The relevant representations may be automatically determined according to the selected chronological medical study and one or more criteria, as discussed previously. The relevant representations may appear in a view within the user interface. The relevant representations may themselves be selected similar to the process discussed in step 830. Selection of a relevant representation may form a selected relevant medical study. A default selection may be provided by the interface, such as defaulting to the study selected in step 830.

At step 850, a thumbnail image may be displayed that corresponds to an image or series of images in the selected relevant medical study. If the study has multiple images or image series, there may be a corresponding display of multiple thumbnail images. The user may initiate preview interactions with the thumbnails to view preview information.

At step 860, an output signal may be supplied to display images, or a series of images (e.g., a cine display of images) on an external monitor. The images may correspond to a thumbnail, a selected thumbnail, the selected relevant medical study, or the selected chronological medical study. At step 870, the images, or series of images may be displayed on a virtual monitor. There may be one or more virtual monitors, and the virtual monitors may reflect a configuration of external monitors. The user may drag and drop the thumbnails, or otherwise select them for display in the virtual monitors. The virtual monitors may provide an opportunity do view images, series of images, movies, etc. from within the user interface.

In addition, the user may be able to perform additional steps (not shown in FIG. 8), including scaling the size of thumbnails, and paging through representations. The thumbnails may be scaled by a slider, or other manners (e.g. right click, drop-down menu, preferences, etc.). Paging may allow the user to view representations that may not fit within one view in a screen.

As an example, method 800 may be performed in the following manner. At step 810, a radiologist opens up a user interface, and enters information corresponding to a patient. The radiologist wishes to review a recently generated cranial CT scan. The CT scan has image data, including several series of information. Each series can be viewed as a movie. In addition to the current CT scan for review, the patient has numerous historical studies, including MRI scans, laboratory exams, and other CT scans. Many of the historical studies are directed to conditions that are not directly related to the patient's current condition.

At step 820, all of the patient's historical studies that are electronically available are displayed in the user interface in a chronological view. The chronological view is near the top of the user interface. The studies are displayed through representations. Each representation has an icon indicative of the study type. The representations also display date and, if the study is an imaging study, the imaging modality. The representations are also color coded, to represent the stage of work-flow processing for each corresponding study. There chronological view is not large enough to contain all of the representations in a single screen view. Therefore, the user has the option of paging through the representations. The chronology view is arranged such that the most recent studies are displayed on the left, and progressively older studies are displayed towards the left. One of the studies is the currently generated cranial CT scan. The radiologist selects with a mouse click the current study to form a selected chronological medical study. To provide visual feedback, the interface enlarges the representation icon to indicate that a selection has been made.

At step 840, the user interface automatically displays a set of relevant studies. The studies are automatically chosen according to the selected chronological medical study, and two relevance criteria: cranial study of the patient, and CT scan of the patient. Thus, the relevant studies include all electronically available cranial CT scans of the patient, including the current study. Each relevant study is displayed as a representation in a view of relevant representations. The view of relevant representations appears below the chronological view, and the representations are displayed in similar chronological form. The radiologist is interested in a prior cranial CT scan, and wishes to view preview information. The radiologist initiates a preview interaction by moving the mouse pointer over the representation. In the proximate vicinity of the representation of interest, preview information pops up. The preview information shows a thumbnail of an image, and also provides other associated data, including the diagnosed condition, and the treating physician. The radiologist determines that this prior study is also of clinical interest for the present condition of the patient. The radiologist then selects the current cranial CT scan from the relevant study view.

At step 850, several thumbnail images appear in a thumbnail view. The thumbnail view is below the relevant study view. Each thumbnail shows a low-resolution image that corresponds to the first image of each series of images in the selected relevant medical study (i.e., the current cranial CT scan). The radiologist then enlarges each thumbnail with a thumbnail scaling slider to better view the thumbnail images. The radiologist now wishes to view a cine view of a particular series in the current cranial CT scan.

At step 870, the radiologist clicks on the thumbnail of the series of interest, and drags and drops it into a virtual monitor. There are two virtual monitors that represent the configuration of external monitors. The radiologist places the thumbnail into the first virtual monitor. At step 860, the same movie feed from the virtual monitor is fed to an external monitor. The radiologist then goes back to step 840, where he selects the relevant representation of the prior study of clinical interest. At step 850, various thumbnails appear corresponding to the various series of images in the prior cranial CT scan. At step 870, the radiologist selects a series, and drags and drops that thumbnail image into the other virtual monitor. The output feed is then provided at step 860 to the other external monitor. The radiologist may then compare the current and prior cranial CT scans by playing back the cine images.

Thus, embodiments of the present invention provide efficient management of clinical patient information. Embodiments of the present invention provide the ability for a clinician to intuitively browse, select, and review the horizontal and vertical patient information. Embodiments of the present invention provide for the clinician to manage in an integrated manner, both horizontally and vertically, the patient history information.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A system for clinical review of a patient, the system comprising:
   a plurality of medical studies stored on at least one memory and relating to a medical history of the patient, wherein each of the plurality of medical studies comprises a representation and metadata;
   a user interface device configured to permit a user to interact with the representations in an application user interface through a user interface device, wherein the application user interface comprises a view of relevant representations;
   a chronology of at least a portion of the representations configured to be displayed through a monitor and the application user interface, wherein each of the displayed representations is configured to be selected by the user to form a selected chronological medical study;
   a processor configured to:
      automatically determine a plurality of relevant representations according to the metadata of the selected chronological medical study and at least one relevance criterion, and
      display the plurality of relevant representations in the view of relevant representations through a monitor;
   wherein the application user interface is configured to automatically populate the view of relevant representations with the plurality of relevant representations;
   wherein each of the plurality of relevant representations is configured to be selected to form a selected relevant medical study; and
   wherein the at least one relevance criterion comprises at least one of a body part, a study type, a treating physician, or a modality.

2. The system of claim 1 further comprising at least one thumbnail image displayed in the application user interface;
   wherein the at least one thumbnail image corresponds to a series of images in the selected relevant medical study; and
   wherein the at least one thumbnail image is configured to be selected to display the series of images in the selected relevant medical study.

3. The system of claim 2 further comprising an external monitor output configured to feed a display of the series of images in the selected relevant medical study to an external monitor.

4. The system of claim 2 further comprising at least one virtual monitor configured to be displayed in the user interface;
   wherein the series of images in the selected relevant medical study is configured to be displayed in the at least one virtual monitor.

5. The system of claim 4, wherein the application user interface is configured to permit the user to drag and drop the at least one thumbnail image into the at least one virtual monitor.

6. The system of claim 1, wherein each of at least a portion of the representations comprises corresponding preview information;
   wherein the user interface device is configured to permit a user to initiate a preview interaction with one of the representations to view the corresponding preview information in the proximate vicinity of the preview interaction.

7. The system of claim 2, wherein the application user interface is adapted to be dynamically configured according to at least one of a thumbnail scale configured to adjust a size of the at least one thumbnail image, or a paging selection configured to page through the representations.

8. The system of claim 1, wherein the plurality of medical studies comprises a radiology study.

9. A method for clinical review of a patient, the method comprising:
   permitting a user to interact with an application user interface through a user interface device, wherein the application user interface comprises a view of relevant representations;
   chronologically displaying chronological representations for a plurality of medical studies relating to a medical history of the patient on a monitor and the application user interface;
   facilitating the user to select, by using the user interface device, one of the chronological representations to form a selected chronological medical study;
   automatically determining a plurality of relevant representations according to metadata of the selected chronological medical study and at least one relevance criterion; and
   automatically populating the view of relevant representations with the plurality of relevant representations through the monitor;
   wherein each of the plurality of relevant representations is configured to be selected to form a selected relevant medical study; and
   wherein the at least one relevance criterion comprises at least one of a date, a range of dates, a body part, a study type, a treating physician, or a modality.

10. The method of claim 9 further comprising displaying at least one thumbnail image in the application user interface, the at least one thumbnail image corresponding to a series of images in the selected relevant medical study, wherein the at least one thumbnail image is configured to be selected and to display the series of images in the selected relevant medical study.

11. The method of claim 10 further comprising feeding an output signal configured to display, on an external monitor, the series of images in the selected relevant medical study.

12. The method of claim 10 further comprising displaying the series of images in the selected relevant medical study through at least one virtual monitor.

13. The method of claim 12 further comprising facilitating the user to drag and drop the at least one thumbnail image into the at least one virtual monitor.

14. The method of claim 9 further comprising displaying preview information for at least one of the chronological representations and at least one of the relevant representations in response to a user-initiated preview interaction.

15. The method of claim 10 further comprising dynamically configuring the application user interface according to at least one of a thumbnail scale configured to adjust a size of the at least one thumbnail image, or a paging selection configured to page through the representations.

16. The method of claim 9, wherein the plurality of medical studies comprises a radiology study.

17. A non-transient computer-readable storage medium including a set of instructions for a computer, the set of instructions comprising:
    an interaction routine configured to permit a user to interact with an application user interface through a user interface device, wherein the application user interface comprises a view of relevant representations;
    a chronological display routine configured to display chronological representations in the application user interface for a plurality of medical studies relating to a medical history of a patient;
    a selection routine configured to facilitate the user to select one of the chronological representations to form a selected chronological medical study;
    a determination routine configured to automatically determine a plurality of relevant representations according to metadata of the selected chronological medical study and at least one relevance criterion; and
    a population routine configured to automatically populate the view of relevant representations with the plurality of relevant representations;
    wherein each of the plurality of relevant representations is configured to be selected to form a selected relevant medical study; and
    wherein the at least one relevance criterion comprises at least one of a date, a range of dates, a body part, a study type, a treating physician, or a modality.

18. The set of instructions of claim 17 further comprising a thumbnail display routine configured to display at least one thumbnail image in the application user interface, wherein the at least one thumbnail image corresponds to a series of images in the selected relevant medical study, and wherein the at least one thumbnail image is configured to be selected and to display the series of images in the selected relevant medical study.

19. The set of instructions of claim 18 further comprising a virtual monitor display routine configured to display the series of images in the selected relevant medical study through at least one virtual monitor.

20. The set of instructions of claim 17 further comprising a preview display routine configured to display preview information for at least one of the chronological representations and at least one of the relevant representations in response to a user-initiated preview interaction.

* * * * *